United States Patent
Oprandi et al.

(10) Patent No.: US 8,533,867 B2
(45) Date of Patent: Sep. 17, 2013

(54) HOSPITAL GARMENT WITH ADJUSTABLE POCKETS

(75) Inventors: Liza Oprandi, Greenland, NH (US); Lucy Reyna, Houston, TX (US)

(73) Assignee: Oprandi & Reyna, LLC, Greenland, NH (US)

( * ) Notice: Subject to any disclaimer, the term of this patent is extended or adjusted under 35 U.S.C. 154(b) by 324 days.

(21) Appl. No.: 12/907,489

(22) Filed: Oct. 19, 2010

(65) Prior Publication Data

US 2012/0090072 A1    Apr. 19, 2012

(51) Int. Cl.
*A41D 10/00*    (2006.01)

(52) U.S. Cl.
USPC .......................................................... 2/114

(58) Field of Classification Search
USPC .................. 2/114, 70, 78.4, 82, 83, 104, 118, 2/119, 125, 126, 138, 141.2, 102; 150/108, 150/113, 144; 190/110, 103
See application file for complete search history.

(56) References Cited

U.S. PATENT DOCUMENTS

| 1,489,046 | A | * | 4/1924 | Thompson | 2/114 |
|---|---|---|---|---|---|
| 2,886,822 | A | * | 5/1959 | Matthews | 2/114 |
| 3,011,172 | A | * | 12/1961 | Tames | 2/51 |
| 3,803,640 | A | * | 4/1974 | Ericson | 2/114 |
| 3,921,221 | A | * | 11/1975 | Zoephel | 2/51 |
| 4,040,124 | A | * | 8/1977 | Zoephel | 2/51 |
| 4,570,268 | A | * | 2/1986 | Freeman | 2/114 |
| 4,612,673 | A | * | 9/1986 | Underhill | 2/114 |
| 4,698,848 | A | * | 10/1987 | Buckley | 2/114 |
| 5,027,438 | A | * | 7/1991 | Schwarze et al. | 2/114 |
| 5,048,122 | A | * | 9/1991 | Prieur | 2/69 |
| 5,361,414 | A | * | 11/1994 | Smith | 2/114 |
| 5,368,920 | A | * | 11/1994 | Schortmann | 442/76 |
| 5,454,376 | A | * | 10/1995 | Stephens et al. | 600/534 |
| D391,038 | S | | 2/1998 | Thompson | |
| 5,991,923 | A | * | 11/1999 | Maria | 2/83 |
| 6,119,270 | A | * | 9/2000 | Chou | 2/108 |
| 6,206,005 | B1 | * | 3/2001 | Keyes | 128/898 |
| 6,460,187 | B1 | * | 10/2002 | Siegel | 2/114 |
| 6,792,622 | B2 | * | 9/2004 | Graves | 2/114 |
| 6,931,875 | B1 | | 8/2005 | Allen | |
| 7,168,103 | B2 | * | 1/2007 | Aldridge et al. | 2/458 |
| 7,181,773 | B1 | * | 2/2007 | Piraka | 2/114 |
| 7,200,871 | B1 | * | 4/2007 | Carlson | 2/103 |
| 7,305,716 | B1 | * | 12/2007 | Richards | 2/114 |
| 7,819,911 | B2 | * | 10/2010 | Anderson et al. | 607/107 |
| 7,823,221 | B2 | * | 11/2010 | Green | 2/114 |

(Continued)

FOREIGN PATENT DOCUMENTS

EP    0507607    * 10/1992

*Primary Examiner* — Shelley Self
*Assistant Examiner* — Catherine M Ferreira
(74) *Attorney, Agent, or Firm* — Mesmer & Deleault, PLLC

(57) ABSTRACT

A hospital garment and method includes a garment fabric having a set of sleeves constructed and arranged to enclose a patient's arms, and a body portion constructed and arranged to enclose a patient's back, chest, and abdomen. The body portion defines a front side corresponding to a region of the body portion constructed and arranged to be worn on top of the patient's chest and abdomen, and an inner surface constructed and arranged to face the patient's back, chest, and abdomen. The hospital garment also includes an adjustable pocket attached to the inner surface of the front side of the body portion. The adjustable pocket defines a left seam, a right seam, a bottom seam, an attaching surface, and a pocket chamber, the adjustable pocket attaching to the inner surface at the attaching surface.

11 Claims, 7 Drawing Sheets

(56) References Cited

U.S. PATENT DOCUMENTS

| | | | |
|---|---|---|---|
| 7,909,150 B2* | 3/2011 | Mangano | 190/103 |
| 8,359,666 B2* | 1/2013 | Appel et al. | 2/114 |
| 2001/0031104 A1* | 10/2001 | Vazquez | 383/2 |
| 2005/0044608 A1* | 3/2005 | Ambrose et al. | 2/114 |
| 2006/0036304 A1 | 2/2006 | Cordani | |
| 2006/0096003 A1* | 5/2006 | Plaatje et al. | 2/114 |
| 2006/0253953 A1* | 11/2006 | Williams | 2/69 |
| 2006/0277655 A1* | 12/2006 | Kerr | 2/114 |
| 2007/0266472 A1* | 11/2007 | DuFaux | 2/80 |
| 2008/0033517 A1 | 2/2008 | Scheberle | |
| 2008/0040831 A1 | 2/2008 | Nilforushan | |
| 2010/0095424 A1* | 4/2010 | Grgich et al. | 2/104 |
| 2010/0205720 A1* | 8/2010 | Ortega Astor | 2/247 |
| 2010/0242150 A1* | 9/2010 | Trouillot | 2/114 |
| 2010/0299802 A1* | 12/2010 | Bailey et al. | 2/70 |
| 2012/0151658 A1* | 6/2012 | Von Furstenberg et al. | 2/114 |
| 2012/0158074 A1* | 6/2012 | Hall | 607/5 |

* cited by examiner

HOSPITAL GARMENT WITH ADJUSTABLE POCKETS

BACKGROUND OF THE INVENTION

1. Field of the Invention

The present invention relates generally to hospital garments. In particular, the invention relates to a hospital garment designed for patients recovering from breast augmentation surgery.

2. Description of the Prior Art

In hospitals, ordinary clothing is often too constrictive for patients about to receive treatment or recovering from treatment. For example, the tight sleeves of a shirt may interfere with a healthcare provider's ability to obtain an accurate pulse reading, or a thick sweater may muffle noises that a healthcare provider may be listening for with a stethoscope. In another example, a pair of jeans may put unnecessary strain on the leg of a patient recovering from knee surgery. To avoid these kinds of issues patients may wear a hospital gown in place of their regular clothes.

Hospital gowns typically are made of fabric (e.g., cotton) that can withstand repeated laundering in hot water and is fastened at the back with twill tape ties. Disposable hospital gowns may be made of paper or thin plastic, with paper or plastic ties. Hospital gowns are much thinner and looser than regular clothing, so patients are less likely to overheat. Patients wearing gowns are also less likely to be bothered by other clothing issues, such as uncomfortable clothing, having to keep multiple changes of clothing on hand, or removing clothing to use the toilet. The gown is significantly easier and more comfortable to move around in than street clothing.

Certain garments such as those described in U.S. Patent Publication No. 2008/0033517 to Scheberle are targeted for patients recovering from breast augmentation surgery. For example, Scheberle describes a garment having inner chambers capable of holding hot or cold therapy packs in the breast and abdominal regions.

SUMMARY OF THE INVENTION

Unfortunately there are deficiencies to the above described conventional hospital gowns. For example, hospital gowns designed for patients recovering from breast augmentation surgery and having chambers for receiving hot or cold therapy packs (such as those described in Scheberle) are not adaptable to accommodate women of different sizes and shapes. In these gowns, chambers that overlay the breasts and abdomen of one woman, may not align properly with another woman (e.g., due to differences in height, width, proportionality, etc.). Additionally, a woman needing to apply hot/cold treatment to one area of the breast or abdomen on one day would be unable to adjust treatment to another area of the breast or abdomen on another day without using a different robe.

Another deficiency to the above described conventional hospital gowns is that due to a single fastening point (e.g., straps in the back or fasteners down the front), a patient is forced to maneuver her arms through the sleeve holes when putting on or removing the gown. For patients recovering from breast augmentation surgery, it may be painful move one's arms in this way to put on or remove the hospital gown.

Additionally, the single fastening point in the back of conventional hospital gowns is insufficient to properly cover up a patient. In particular patients may feel embarrassed to walk around with portions of their backside exposed. This problem is magnified if devices such as IV tubes are run through the rear opening of the conventional hospital gown.

Yet another deficiency to the above described conventional hospital gowns is that they are not very attractive.

In contrast to the above described conventional hospital gowns, an improved hospital/bed garment is configured as a stylish bed jacket having closable openings down the front and sides of the jacket. This allows the garment to be wrapped around a patient and fastened together so that the patient does not need go through the painful motion of inserting her arms into and out of sleeves post-surgery. Unlike conventional hospital gowns, the present invention covers a user's entire backside, which is particularly important when a patient moves about the hospital such as walking down the halls as part of the patient's course of healing or when attached to an IV pump, or when requiring medical testing where the patient must wait in semi-public or public waiting areas. Additionally, the closable openings allow a patient to be fully covered even when devices such as IV tubes are passed through them. The improved hospital/bed garment also includes one or more pockets that may hold treatment packs (e.g., hot/cold therapy packs, medical monitoring devices, etc.) and whose depth can be adjusted by folding and fastening each pocket to itself. This allows the location of, for example, hot/cold therapy to be adjusted to a desired location on a patient's body without removing the garment. Each of the one or more pockets may be permanently fixed to a predefined location on the inside surface of the garment or may optionally be removably attached to the inside surface of the garment. Additionally, due to the multiple openings down the front and side of the jacket, the one or more pockets when provided as removable pockets can easily be added, removed, or adjusted from multiple locations. These multiple access points minimize the possibility that the patient may need to move to access the removable pockets. Particularly, the present invention not only assists in the healing process of user's/patient's requiring hot/cold therapy and/or monitoring of specific body parameters but also provides a sense of dignity to the user.

For example, one embodiment is directed to a hospital garment. The hospital garment includes a fabric having a set of sleeves constructed and arranged to enclose a patient's arms, and a body portion constructed and arranged to enclose a patient's back, chest, and abdomen. The body portion defines a front side corresponding to a region of the body portion constructed and arranged to be worn on top of the patient's chest and abdomen, and an inner surface constructed and arranged to face the patient's back, chest, and abdomen. The hospital garment also includes a set of adjustable pockets attached either permanently or removably to the inner surface of the front side of the body portion. Each adjustable pocket defines a left seam, a right seam, a bottom seam, an attaching surface, and a pocket chamber. Each adjustable pocket attaches to the inner surface at the attaching surface. The pocket chamber is constructed and arranged to hold temperature therapy packs. Each adjustable pocket includes a set of pocket adjusting fasteners on the left seam and the right seam. Each adjustable pocket is constructed and arranged to adjust the depth of the pocket chamber by attaching together two of the pocket adjusting fasteners on the left seam and two of the pocket adjusting fasteners on the right seam.

It is further contemplated that the hospital/bed garment of the present invention is not gender specific and is provided in various lengths to suit the patient, medical procedure, etc. The outer surface of the hospital/bed garment may have stylish designs that are gender neutral or specific to a patient's gender and age.

In another embodiment of the present invention, there is provided a method of making the hospital garment. The method includes providing a garment fabric having (i) a set of sleeves constructed and arranged to enclose a patient's arms, and (ii) a body portion constructed and arranged to enclose a patient's back, chest, and abdomen, the body portion defining a front side corresponding to a region of the body portion constructed and arranged to be worn on top of the patient's chest and abdomen, and an inner surface constructed and arranged to face the patient's back, chest, and abdomen, and providing an adjustable pocket attached to the inner surface of the front side of the body portion, the adjustable pocket defining a left seam, a right seam, a bottom seam, an attaching surface, and a pocket chamber, the adjustable pocket attaching to the inner surface at the attaching surface, the pocket chamber constructed and arranged to hold treatment packs where the adjustable pocket includes a set of pocket adjusting fasteners on the left seam and the right seam and where the adjustable pocket is constructed and arranged to adjust the depth of the pocket chamber by attaching together two of the pocket adjusting fasteners on the left seam and two of the pocket adjusting fasteners on the right seam.

In a further embodiment, the method includes providing an adjustable and removable pocket attached to the inner surface of the front side of the body portion.

In still another embodiment of the present invention, the method includes providing a first sleeve hem removably attachable to a second sleeve hem and a first back portion hem removably attachable to a first front portion hem wherein the first back portion hem and the first front portion hem are substantially parallel to a longitudinal axis of the body portion.

DETAILED DESCRIPTION OF THE PREFERRED EMBODIMENT

The preferred embodiment(s) of the present invention is illustrated in FIGS. 1-7.

An improved hospital garment is configured as a stylish bed jacket for use in hospitals, assisted living facilities, spas, etc. The hospital garment has closable openings down the front and sides of the jacket. This allows the garment to be wrapped around a patient and fastened together so that the patient does not need go through the painful motion of inserting her arms into and out of sleeves post-surgery. Additionally, the closable openings allow a patient to be fully covered even when devices such as IV tubes are passed through them. The improved hospital garment also includes removable pockets that hold treatment packs (e.g., hot/cold therapy packs, medical monitoring devices, etc.) and whose depth can be adjusted by folding and fastening each removable pocket to itself. This allows the location of, for example, hot/cold therapy to be adjusted to a desired location on a patient's body without removing the garment. Additionally, due to the multiple openings down the front and side of the jacket, the removable pockets can easily be added, removed, or adjusted from multiple locations. These multiple access points minimize the possibility that the patient may need to move to access the removable pockets.

Figure 1:
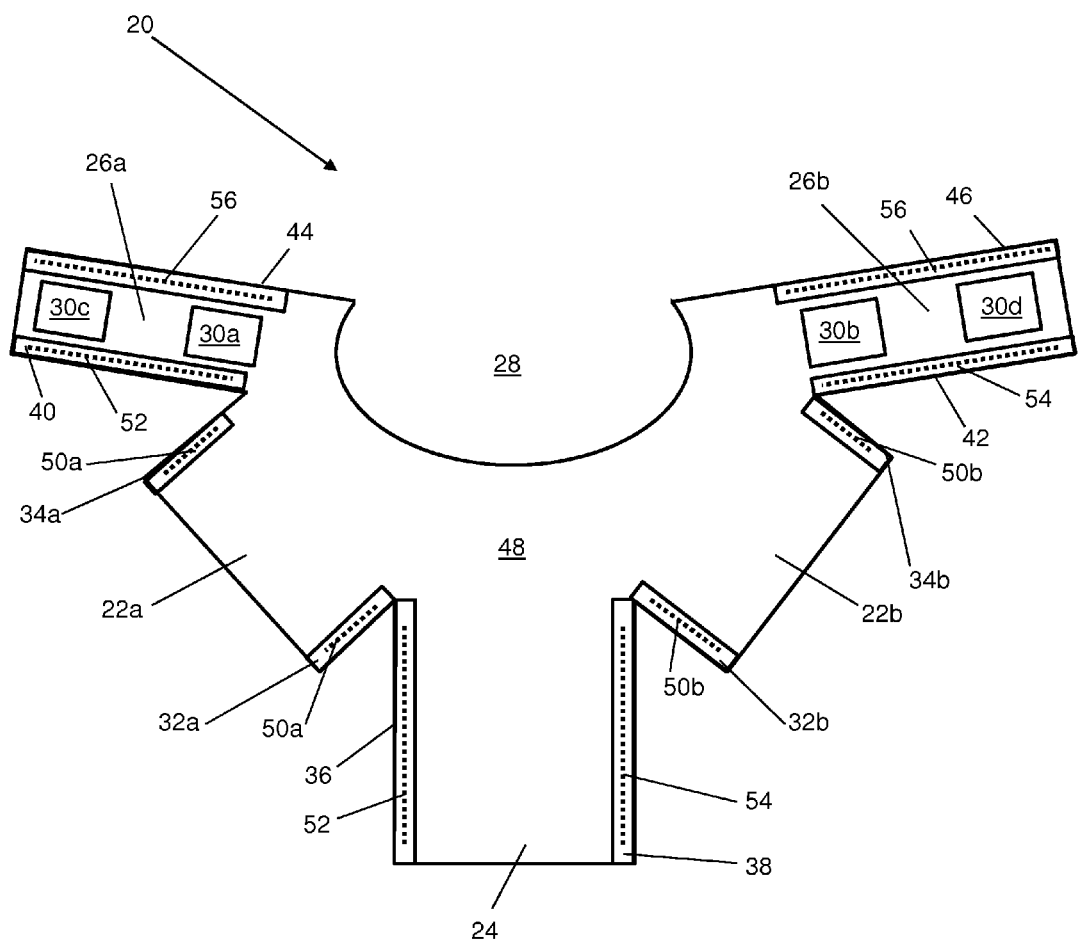
FIG. 1 is a front view of a garment in an unattached configuration.

FIG. 1 shows a garment 20 (i.e., hospital garment or bed jacket) in an unattached configuration. The garment 20 includes a set of sleeves 22 (i.e., left sleeve 22a and right sleeve 22b), a back portion 24, a left front portion 26a, a right front portion 26b (the left front portion 62a and the right front portion 26b forming a front portion 26), a head opening 28, and a set of adjustable pockets 30 (i.e., one or more adjustable pockets 30a, 30b, 30c, 30d).

As seen in FIG. 1, the each sleeve 22a, 22b includes a first sleeve hem 32a, 32b and a second sleeve hem 34a, 34b. The back portion 24 includes a first back portion hem 36 and a second back portion hem 38. The front portion 26 includes a first front portion hem 40, a second front portion hem 42, a third front portion hem 44, and a fourth front portion hem 46.

The first sleeve hem 32a, 32b and the second sleeve hem 34a, 34b includes a set of sleeve fasteners 50. The first back portion hem 36 and the first front portion hem 40 include a set of first body portion fasteners 52. The second back portion hem 38 and the second front portion hem 42 includes a set of second body portion fasteners 54. The third front portion hem 44 and the fourth front portion hem 46 include set of third body portion fasteners 56. The various fasteners 50, 52, 54, 56 may be of any suitable type for securing the garment 20 to itself. Example fasteners include hook and loop connectors, snaps, buttons, ties, zippers, etc.

The garment 20 defines an inner surface 48 that is constructed and arranged to face the patient when the garment 20 is being worn. The set of adjustable pockets 30 removably attach to the inner surface 48 of the front portion 26 of the garment 20. The set of adjustable pockets 30 constructed and arranged to hold hot/cold therapy packs and are positioned to apply hot/cold therapy from these packs to the abdominal and chest regions of the patient. For example, for a patient recovering from breast augmentation surgery, upper pockets 30a, 30b are positioned to apply hot/cold therapy to the patient's breasts and lower pockets 30c, 3d are positioned to apply hot/cold therapy to a patient's abdomen. Since the adjustable pockets 30 are removably attached to the inner surface 48 of the garment 20, the pockets 30 may be added or removed as needed. For example, if therapy is no longer needed on the abdomen, but still needed on the breasts, lower pockets 30c, 30d may be removed while leaving the upper pockets 30a, 30b in place.

When putting on the garment 20, the garment 20 drapes over the patient with the inner surface 48 of the back portion 24 laying on top of the patient's back and the head opening 28 positioned around the patient's neck. Additionally, the sleeves 22a, 22b drape over the patient's arms. Since it can be painful for a patient to move after breast augmentation surgery, an assistant (e.g., health care provider, relative, etc.) may be the one to drape the garment 20 over the patient while the patient sits still.

Figure 2:
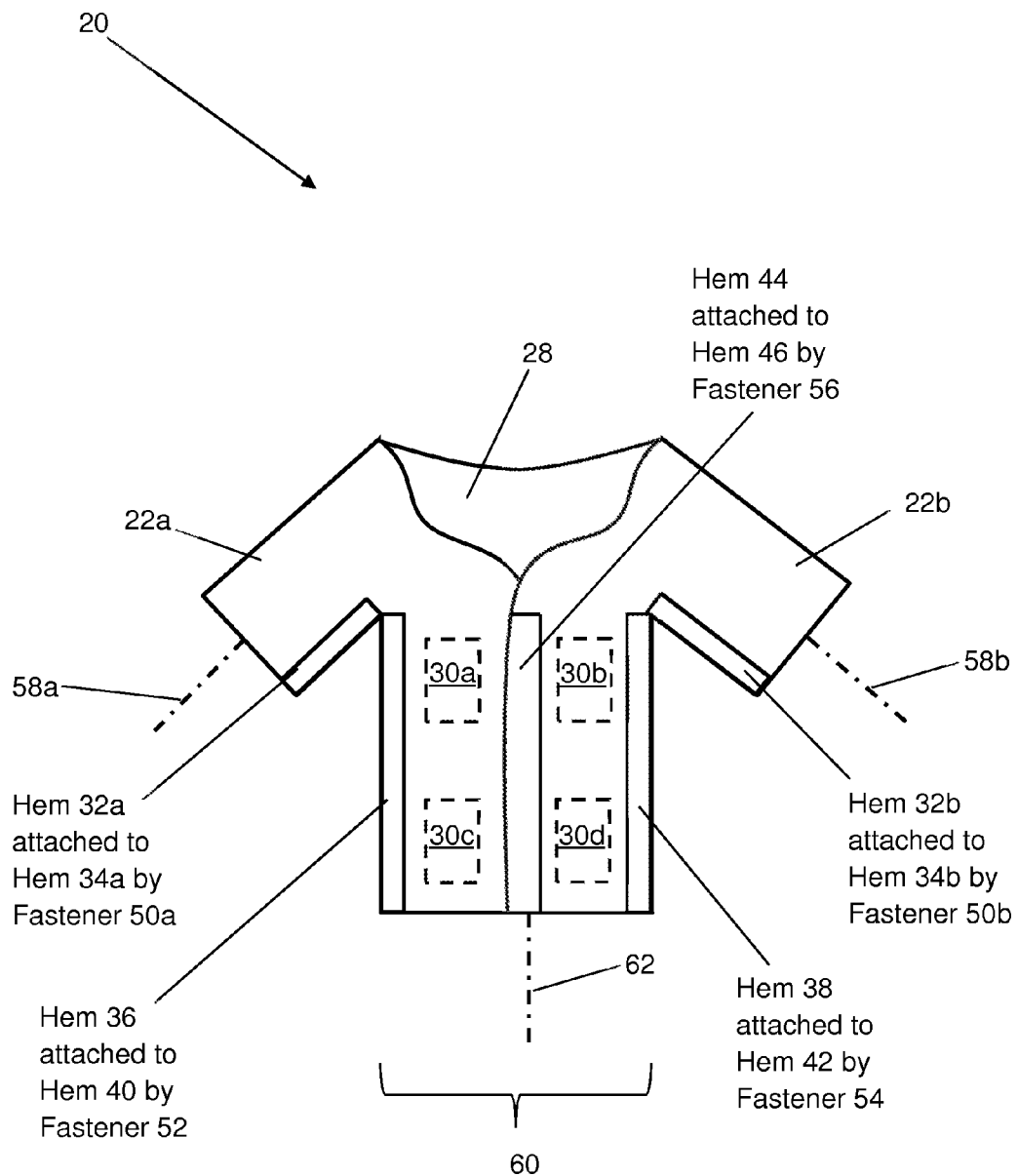
FIG. 2 is a front view of the garment of FIG. 1 in an attached configuration.

FIG. 2 shows the garment 20 in an attached configuration. To attach the garment 20 together the various sets of fasteners 50, 52, 54, 56 are used to attach the various hems 34, 36, 38, 40, 42, 44, 46 of the garment 20 together. In particular, the set of sleeve fasteners 50 are used to attach the first sleeve hem 32 to the second sleeve hem 34. The set of first body portion fasteners 52 are used to attach the first back portion hem 36 to the first front portion hem 40. The set of second body portion fasteners 54 are used to attach the second back portion hem 38 to the second front portion hem 42. The set of third body portion fasteners 56 are used to attach the third body portion hem 44 to the fourth body portion hem 46.

Upon attaching the first sleeve hem 32 to the second sleeve hem 34 with the set of sleeve fasteners 50, the sleeve 22 forms a substantially cylindrical shape about a sleeve axis 58 (i.e., where the patient's arm is). The first sleeve hem 32 and the second sleeve hem 34 are aligned substantially parallel to the sleeve axis 58.

Upon attaching front portion 26 and the back portion 24 together with the body portion fasteners 52, 54, 56, the front portion 26 and back portion 24 form a body portion 60 in a substantially cylindrical shape about a body portion axis 62 (i.e., where the patient's midsection is). The first back portion hem 36, the second back portion hem 38, the first front portion hem 40, the second front portion hem 42, the third front portion hem 44, and the fourth front portion hem 46 are aligned substantially parallel to the body portion axis 62.

When adding, removing, or otherwise adjusting the adjustable pockets 30, there are multiple access points. For example, when accessing the adjustable pocket 30a providing hot/cold therapy to the patient's right breast, access is achieved by temporarily undoing the first body portion fasteners 52 and/or the third body portion fasteners 56. Additionally access to pocket 30a can be achieved by accessing through the head opening 28. In another example, when accessing the adjustable pocket 30d providing hot/cold therapy to the patient's left abdominal region, access is achieved by temporarily undoing the second body portion fasteners 54 and/or the third body portion fasteners 56.

Figure 3:
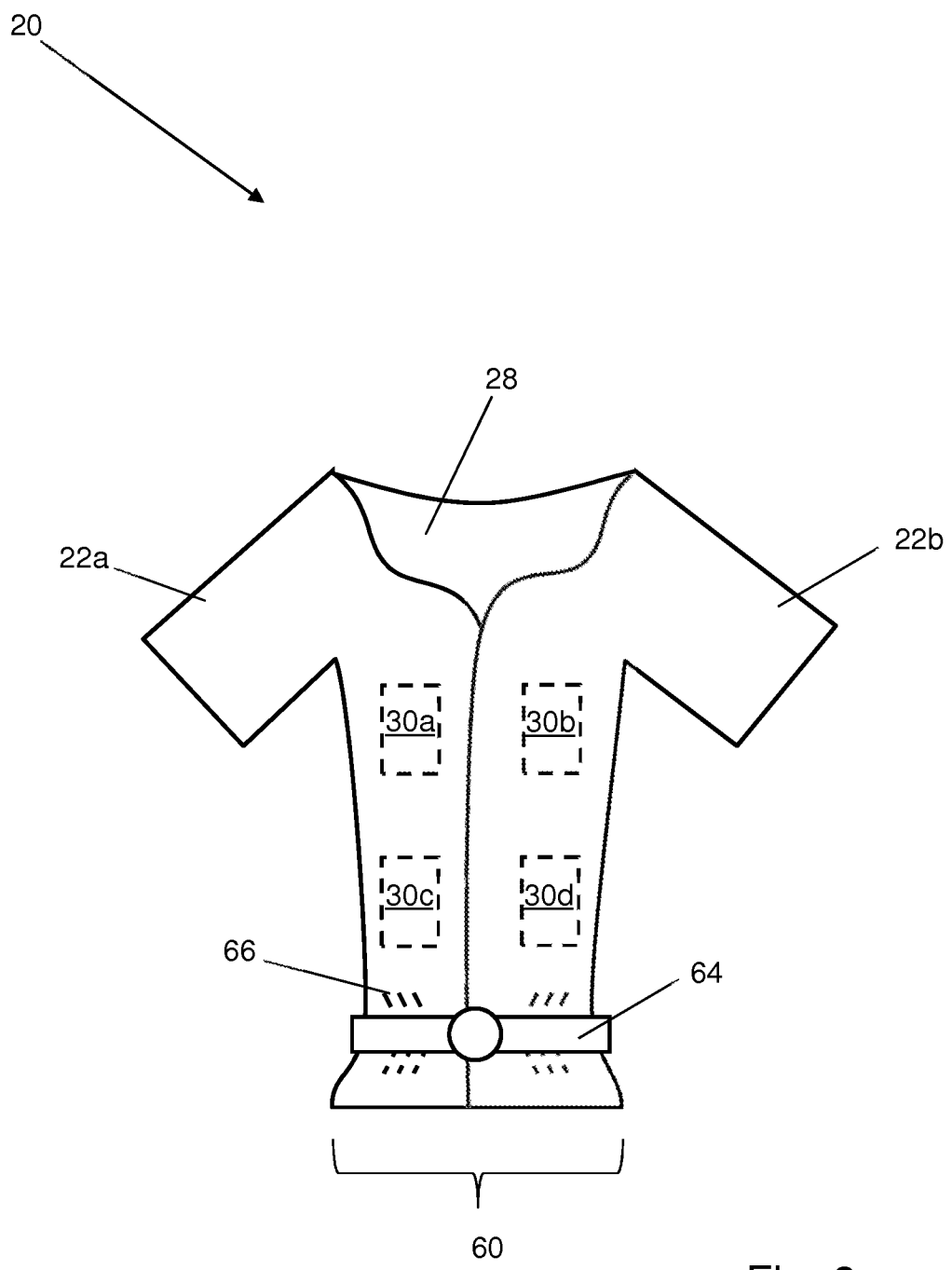
FIG. 3 is a front view of another embodiment of the garment of FIG. 1.

In some arrangements, the garment 20 includes enhancements to improve its overall aesthetic appearance. For example, as seen in FIG. 3, the garment 20 includes smocking 64 and a belt 66 around the waist area of the garment 20.

Figures 4A, 4B:
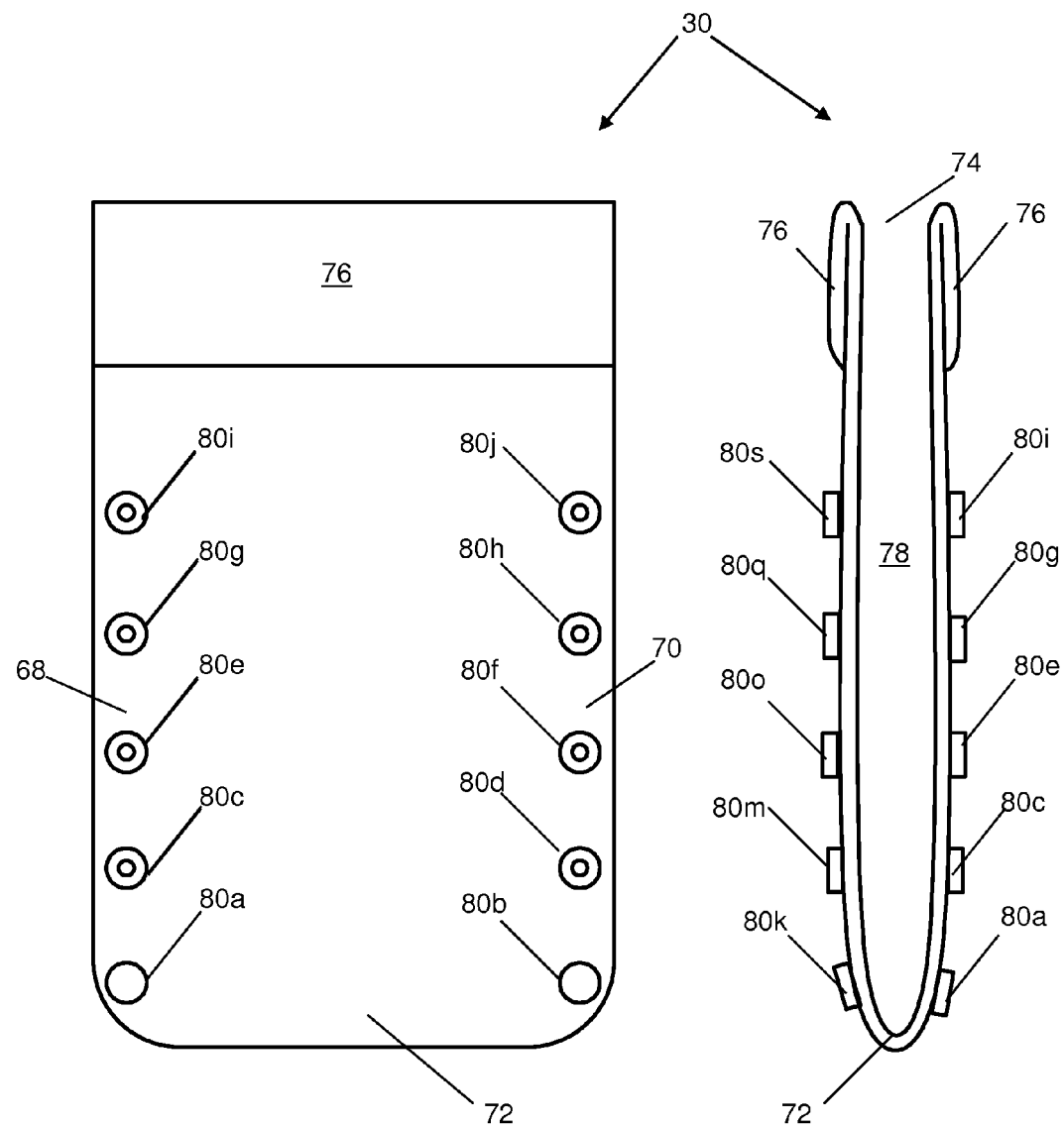
FIG. 4a is a front view of an adjustable pocket of the garment of FIG. 1.
FIG. 4b is a cutaway side view of an adjustable pocket of the garment of FIG. 1.

FIGS. 4a-4b show the adjustable pocket 30. The adjustable pocket 30 includes a first side seam 68, a second side seam 70, a bottom seam 72, a top opening 74, an attaching surface 76, a pocket chamber 78 and a plurality of pocket adjusting fasteners 80.

The adjustable pocket 30 is constructed and arranged to attach to the inner surface 48 of the garment 20 at the attaching surface 76. The attaching surface may removably attach to the inner surface 48 of the garment 20 in any suitable way. For example, removable attachment may be accomplished using Hook and loop connectors, snaps, buttons, clips, pins, etc.

The pocket chamber 78 is constructed and arranged to receive hot/cold therapy packs via the top opening 74. In some arrangements, the pocket chamber 78 is lined with a water proof material (i.e., plastic) to prevent condensation or other wetness from the hot/cold therapy packs from seeping through to the skin of the patient.

The plurality of pocket adjusting fasteners 80 are distributed on an outer surface of the adjustable pocket 30 (e.g., along the first side seam 68 and the second side seam 70). The pocket adjusting fasteners 80 may be of any suitable type (e.g., Hook and loop connectors, snaps, buttons, clips, pins, etc.) for fastening one portion of the adjustable pocket 30 to another part of the adjustable pocket.

Figures 5A, 5B:
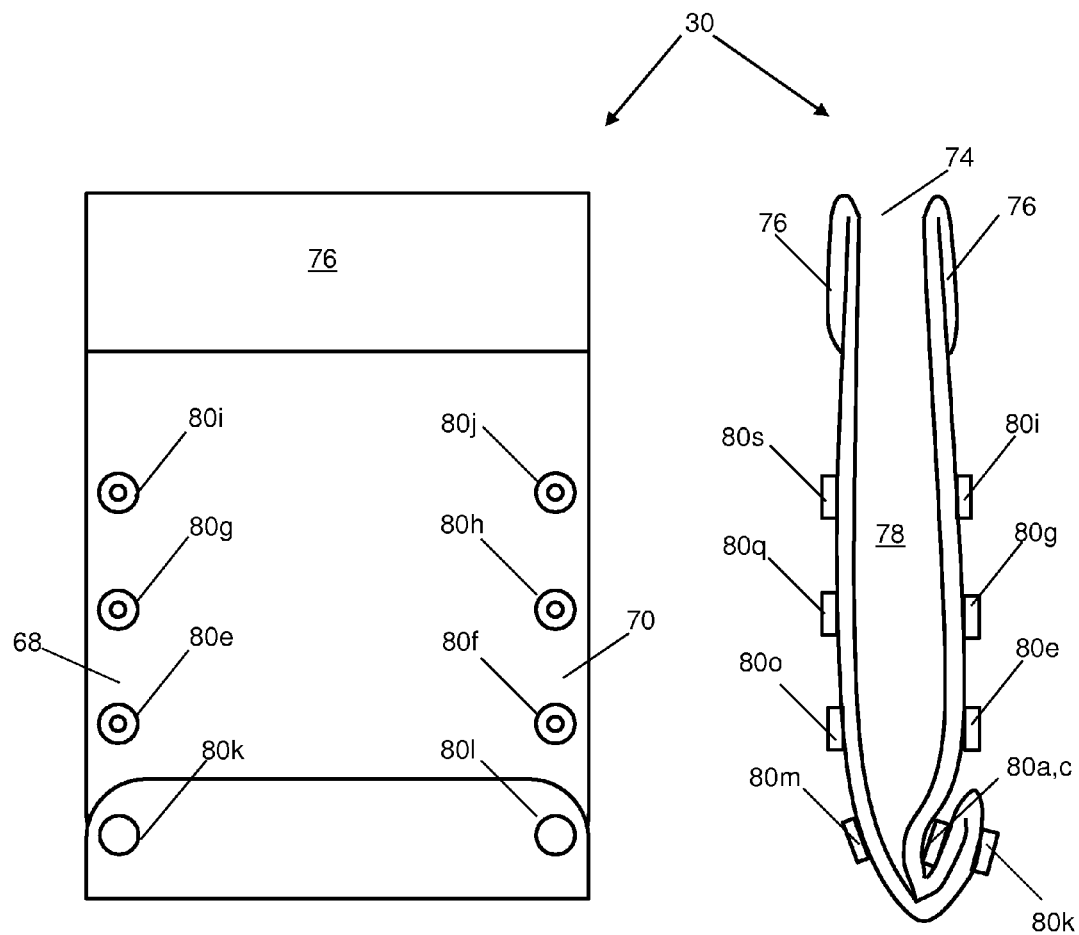
FIG. 5a is a front view of an adjustable pocket of the garment of FIG. 1.
FIG. 5b is a cutaway side view of an adjustable pocket of the garment of FIG. 1.
Figures 6A, 6B:
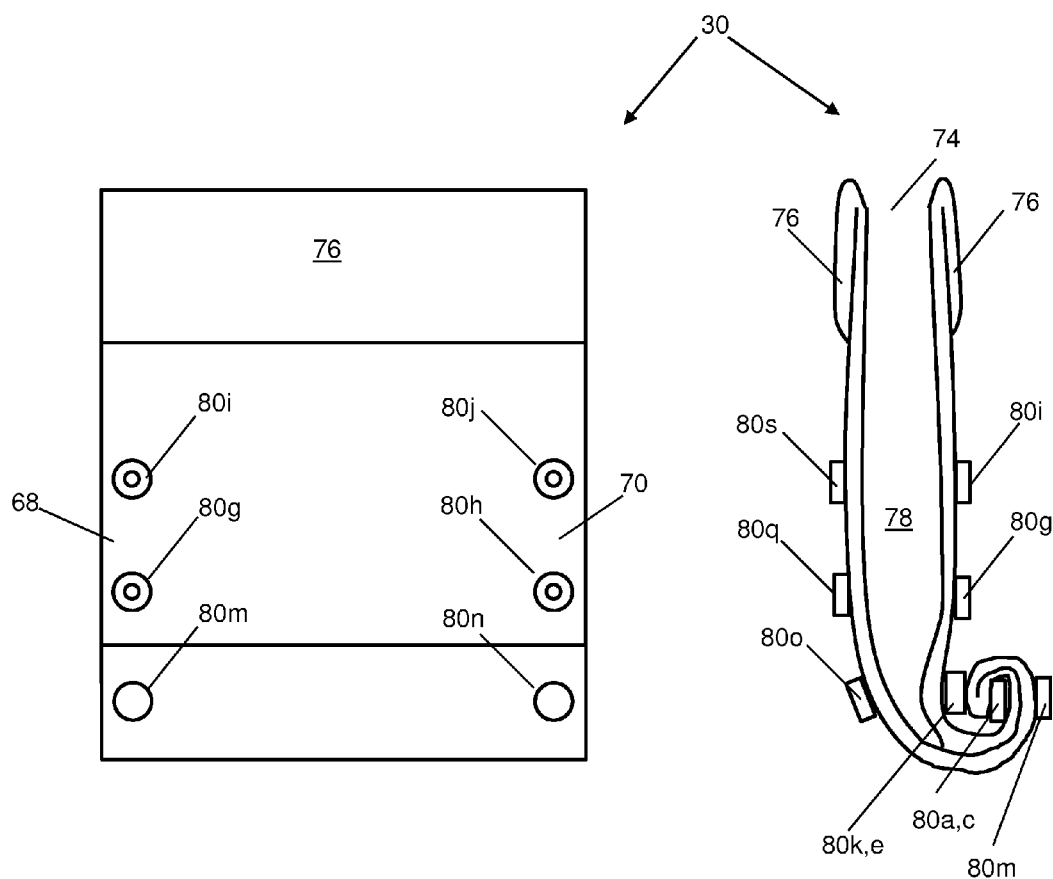
FIG. 6a is a front view of an adjustable pocket of the garment of FIG. 1.
FIG. 6b is a cutaway side view of an adjustable pocket of the garment of FIG. 1.
Figures 7A, 7B:
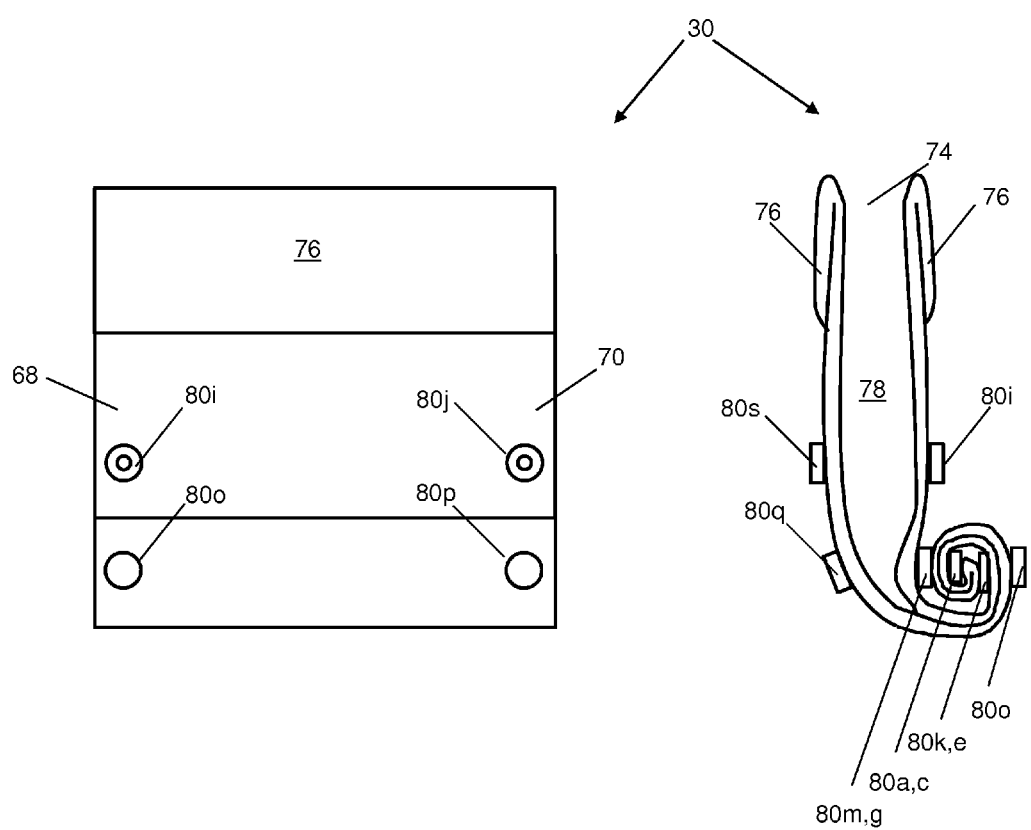
FIG. 7a is a front view of an adjustable pocket of the garment of FIG. 1.
FIG. 7b is a cutaway side view of an adjustable pocket of the garment of FIG. 1.

In use, as seen in FIGS. 5a-5b, if a patient wishes to adjust the depth of the pocket 30 to raise the positioning of the hot/cold therapy packs, the bottom seam 72 is folded upwards and fasteners 80 from a lower part of the pocket 30 attach to fasteners 80 on a higher part of the pocket. For example, a lower fastener 80a along the first side seam 68 is attached to a higher fastener 80c along the first side seam 68, and a lower fastener 80b along the second side seam 70 is attached to a higher fastener 80d along the second side seam 70. Thus the depth of the bottom of the usable pocket chamber 78 is raised from a lower height to a higher height. Conversely, the process may be reversed to adjust the depth of the pocket 30 to lower the positioning of the hot/cold therapy packs.

In some arrangements, the depth of the pocket 30 is adjusted further by continuing to roll up the pocket 30 and affixing additional fasteners 80 together as seen in FIGS. 6a-7b.

The adjustable depth of the pocket 30, for example with regard to patients recovering from breast augmentation surgery, allow for precise targeting of hot/cold therapy to precisely the region of the breast or abdomen requiring treatment.

Other aspects of the invention may include a top layer that has stain resistant wrinkle free material with attractive print and an optional inner layer of a thin fleece or heavy cotton to provide warmth. Hospitals, assistant living communities, etc. are commonly cold facilities. The inner layer will provide warmth and comfort for users. Additionally, the fabric is preferably washable. The smocking is sewn at the waist to give hospital garment shape and is typically 2 to 3 inches wide and 2 to 3 inches long. The hospital garment may also have other characteristics such as embellished collars, sleeves and a belt with different lengths of hems; short (to mid thigh), med (knee length) and long (to mid calf). The overall length of the hospital garment may vary to accommodate different styles.

For example, while the hospital garment has been described for use in treating patients recovering from breast augmentation surgery, this is not the only application. The hospital garment may be used by men or women to treat any condition that requires targeted therapy on a patient's body.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A hospital garment comprising:
 a garment fabric having (i) a set of sleeves constructed and arranged to enclose a patient's arms, and (ii) a body portion constructed and arranged to enclose a patient's back, chest, and abdomen, the body portion defining a front side corresponding to a region of the body portion constructed and arranged to be worn on top of the patient's chest and abdomen, and an inner surface constructed and arranged to face the patient's back, chest, and abdomen; and
 an adjustable pocket attached to the inner surface of the front side of the body portion, the adjustable pocket defining a left seam, a right seam, a bottom seam, an attaching surface, and a pocket chamber, the adjustable pocket attaching to the inner surface at the attaching surface, the pocket chamber constructed and arranged to hold treatment packs;
 wherein the adjustable pocket includes a set of pocket adjusting fasteners on the left seam and the right seam;

wherein the adjustable pocket is constructed and arranged to adjust the depth of the pocket chamber by attaching two of the set of pocket adjusting fasteners on the left seam to each other and two of the set of pocket adjusting fasteners on the right seam to each other.

2. The hospital garment of claim 1:
wherein each sleeve includes a first sleeve hem and a second sleeve hem, the first sleeve hem and the second sleeve hem being substantially parallel to a longitudinal axis of the sleeve;
wherein the body portion further defines a back side corresponding to a region of the body portion constructed and arranged to be worn on top of the patient's back;
wherein the back side of the body portion includes a first back portion hem and a second back portion hem, the first back portion hem and the second back portion hem being substantially parallel to a longitudinal axis of the body portion;
wherein the front side of the body portion includes a first front portion hem, a second front portion hem, a third front portion hem, and a fourth front portion hem, the first front portion hem, the second front portion hem, the third front portion hem, and the fourth front portion hem being substantially parallel to the axis of the body portion;
wherein the first sleeve hem is removably attached to the second sleeve hem with a set of sleeve fasteners, the first back portion hem is removably attached to the first front portion hem with a set of first body portion fasteners, the second back portion hem is removably attached to the second front portion hem with a set of second body portion fasteners, and the third front portion hem is attached to the fourth front portion hem with a set of third body portion fasteners.

3. The hospital garment of claim 1 wherein the body portion includes smocking constructed and arranged to reduce a circumference of the body portion along a waist area to give the garment a stylish appearance.

4. The hospital garment of claim 1 wherein further comprising a belt positioned around the waist area of the body portion.

5. The hospital garment of claim 1:
wherein the pocket chamber is lined with a waterproof material constructed and arranged to prevent moisture from the treatment packs from leaking through the adjustable pocket to the patient.

6. A method of making a garment comprising:
providing a garment fabric having (i) a set of sleeves constructed and arranged to enclose a patient's arms, and (ii) a body portion constructed and arranged to enclose a patient's back, chest, and abdomen, the body portion defining a front side corresponding to a region of the body portion constructed and arranged to be worn on top of the patient's chest and abdomen, and an inner surface constructed and arranged to face the patient's back, chest, and abdomen; and
providing an adjustable pocket attached to the inner surface of the front side of the body portion, the adjustable pocket defining a left seam, a right seam, a bottom seam, an attaching surface, and a pocket chamber, the adjustable pocket attaching to the inner surface at the attaching surface, the pocket chamber constructed and arranged to hold treatment packs;
wherein the adjustable pocket includes a set of pocket adjusting fasteners on the left seam and the right seam;
wherein the adjustable pocket is constructed and arranged to adjust the depth of the pocket chamber by attaching two of the set of pocket adjusting fasteners on the left seam to each other and two of the set of pocket adjusting fasteners on the right seam to each other.

7. The method of claim 6, wherein the adjustable pocket is removably attached to the inner surface.

8. The method of claim 6, further comprising:
providing a first sleeve hem removably attachable to a second sleeve hem; and
providing a first back portion hem removably attachable to a first front portion hem;
wherein the first back portion hem and the first front portion hem are substantially parallel to a longitudinal axis of the body portion.

9. The method of claim 8 further comprising positioning the first sleeve hem and the second sleeve hem along an inside of each of the set of sleeves.

10. The method of claim 8, further comprising providing a second back portion hem removably attachable to a second front portion hem wherein the second back portion hem and the second front portion hem are substantially parallel to a longitudinal axis of the body portion.

11. The method of claim 10, further comprising providing a third front portion hem and a fourth front portion hem defining the front portion into a left front portion and a right front portion wherein the third front portion hem and the fourth front portion hem are substantially parallel to a longitudinal axis of the body portion.

\* \* \* \* \*